(12) United States Patent
Van Erum

(10) Patent No.: US 10,460,620 B2
(45) Date of Patent: Oct. 29, 2019

(54) DEVICE FOR LINKING BODILY MOVEMENT TO LEARNING BEHAVIOUR AND METHOD WHEREBY SUCH A DEVICE IS APPLIED

(71) Applicant: VANERUM BELGIE NV, Diest (BE)

(72) Inventor: Gert Van Erum, Diest (BE)

(73) Assignee: I3-TECHNOLOGIES, NAAMLOZE VENNOOTSCHAP, Deerlijk (BE)

( * ) Notice: Subject to any disclaimer, the term of this patent is extended or adjusted under 35 U.S.C. 154(b) by 198 days.

(21) Appl. No.: 15/405,468

(22) Filed: Jan. 13, 2017

(65) Prior Publication Data

US 2017/0206796 A1    Jul. 20, 2017

(30) Foreign Application Priority Data

Jan. 14, 2016  (BE) .................................. 2016/5021

(51) Int. Cl.
| | |
|---|---|
| *G09B 7/06* | (2006.01) |
| *A61B 5/00* | (2006.01) |
| *A61B 5/11* | (2006.01) |
| *A47B 39/08* | (2006.01) |
| *A47C 7/18* | (2006.01) |
| *A47C 7/72* | (2006.01) |
| *A47C 11/00* | (2006.01) |

(52) U.S. Cl.
CPC ................ *G09B 7/06* (2013.01); *A47B 39/08* (2013.01); *A47C 7/18* (2013.01); *A47C 7/72* (2013.01); *A47C 7/725* (2013.01); *A47C 11/005* (2013.01); *A61B 5/002* (2013.01); *A61B 5/1104* (2013.01); *A61B 5/6891* (2013.01); *A61B 5/1116* (2013.01); *A61B 5/742* (2013.01); *A61B 2503/06* (2013.01)

(58) Field of Classification Search
CPC ..... A61B 5/6891; A61B 5/002; A61B 5/1104; A61B 5/742; A61B 5/1116; A61B 2503/06; A47C 11/005; A47C 7/18; A47C 7/72; A47C 7/725; A47B 39/08; G09B 7/06

See application file for complete search history.

(56) References Cited

U.S. PATENT DOCUMENTS

| | | | | |
|---|---|---|---|---|
| 2001/0048372 | A1* | 12/2001 | Tomich .................. | G08B 21/02 340/689 |
| 2012/0015334 | A1* | 1/2012 | Hamilton ........... | A63B 71/0622 434/247 |
| 2012/0329018 | A1* | 12/2012 | Katz ..................... | G06Q 50/22 434/236 |
| 2017/0148340 | A1* | 5/2017 | Popa-Simil .............. | G09B 9/48 |

\* cited by examiner

*Primary Examiner* — Nathan Hillery
(74) *Attorney, Agent, or Firm* — Young & Thompson

(57) ABSTRACT

Device for linking bodily movement to learning behaviour, whereby this device (1) consists of a number of objects that can be used by pupils as flexible adjustable seating units (2), characterised in that these seating units are each equipped with a digital module (4) that is able to detect movements of the seating unit caused by the pupils, and to communicate these movements wirelessly to a central teaching module (3), after which the central teaching module (3) can wirelessly send back an individual message to each of the seating units (2), adapted to the movement that is made with each of the seating units.

12 Claims, 5 Drawing Sheets

DEVICE FOR LINKING BODILY MOVEMENT TO LEARNING BEHAVIOUR AND METHOD WHEREBY SUCH A DEVICE IS APPLIED

BACKGROUND OF THE INVENTION

Field of the Invention

The present invention relates to a device for linking bodily movement to learning behaviour and a method whereby such a device is applied.

More specifically the invention is intended for encouraging the learning behaviour of children by linking learning behaviour to bodily movement by the learning child in an educational environment.

Description of the Related Art

It is known that children learn something more quickly when the learning is linked to active bodily movement such that better associations can be made.

Traditionally education is taught ex cathedra, whereby the pupils are limited in their freedom of movement such as at a school desk for example, and they frequently have to listen passively to what is presented to them, without making any appreciable movement, or being able to utilise the full space of the classroom.

Such a learning environment leads to waning attention, boredom, reduced creativity and less teamwork, and to a longer learning process in order to learn the desired thing.

A disadvantage of traditional educational practices is that the available space cannot be utilised flexibly, but is bound to the traditional arrangement of rows of school desks or tables with chairs and a teacher at the front, mostly on a raised step above which there is a blackboard for presenting the subject matter.

BRIEF SUMMARY OF THE INVENTION

The purpose of the present invention is to provide a solution to the aforementioned and other disadvantages, by providing a device that encourages the learning process by linking bodily movement to learning behaviour and through the more flexible utilisation of the available educational space.

To this end the invention concerns a device for linking bodily movement to learning behaviour, whereby this device consists of a number of objects that can be used by pupils as flexible adjustable seating units, whereby these seating units are each equipped with a digital module that is able to record movements of the seating unit and to communicate this movement wirelessly to a central teaching module, after which the central teaching module can wirelessly send back an individual message to each of the seating units, adapted to the movement that is made with each of the seating units.

An advantage of such a device is that the seating units can be arranged in a number of ways in a room, and moreover can be placed in different positions.

Another advantage of such a device is that it enables the group of pupils to be asked a question that they have to answer, and this by moving their seating unit, for example by turning a chosen side of the seating unit upwards. In this way the pupil can make his choice known from a number of possible answers, by making the desired movement with his seating unit, for example by turning the desired side upwards.

The digital module in the seating unit detects which side is now on top and sends this information wirelessly to the central teaching module, which then assesses the answer and wirelessly sends a different message to each seating unit depending on whether the answer is right or wrong.

Preferably the seating unit is equipped with one or more light sources that can be switched on or off by the central teaching module, and whose colour can be changed by the central teaching module.

An advantage of such light sources is that they are able to reproduce a message from the central teaching module by means of the light signal, whose colour can also provide information to the user of the seating unit, for example whether he has given a correct (green light) or incorrect (red light) answer to a question that has been put to all pupils.

Preferably the light sources are integrated in the digital module, and the digital module shows the light signal on a surface of the seating unit.

An advantage of such a digital module is that it can be affixed in the seating unit, but that it also shows a visible light signal to the user of the seating unit on the surface of the seating unit.

Preferably the digital module is provided with a battery that can be charged by means of a charger from the public electricity network or another power source.

An advantage of such a battery is that the seating unit can be moved autonomously and requires no cabling, in order to have an operating digital module.

Preferably the seating unit is cube-shaped whereby the cube shape can be regular or irregular.

An advantage of an irregular cube shape is that the pupil can place it on the floor in different ways. In this way the pupil can turn a convex side towards the floor, and let the cube rock back and forth by bodily movement.

Preferably the irregular cube shape enables the seating units to be placed together with the formation of a circle, a semicircle or other geometric figures around the central teaching module.

An advantage of such an arrangement is that each pupil is just as far away from the central teaching module and cannot be obstructed by other pupils. In this arrangement a teacher has a good overview of all pupils who all occupy an equivalent position.

Preferably the seating unit is made of an energy absorbing synthetic foam, such as expanded polypropylene (EPP) for example.

An advantage of an embodiment in synthetic foam is that this material is able to reversibly accommodate static or dynamic loads, which enables the seating units not only to be used as a seating unit on all sides, but it can also be moved by throwing it in the air for example, or by knocking it with a hand or foot, etc.

Another advantage of an embodiment in synthetic foam is that the seating unit can be produced by injection moulding, and that the weight of the seating unit is very low, so that children or pupils can easily lift or move the seating unit.

Preferably the seating units are each equipped with movement detectors, i.e. accelerometers and orientation detectors that are connected to the digital module of the seating unit and pass on the observed movements and positions to the digital module of the seating unit.

An advantage of these movement detectors is that the digital module of the seating unit knows at all times which side of the cube is oriented upwards for example, or that the seating unit has been shaken for example, and can also pass on this information to the central teaching module.

Preferably the movement detectors of each seating unit can detect which side of the seating unit is oriented upwards, or whether the seating unit has been knocked by a hand or foot for example, and the number of times it has been knocked, or whether the seating unit has been thrown in the air by free-fall detection, or the seating unit has been shaken and the number of times that it has been shaken, or whether the seating unit is rocking back and forth, for example by moving back and forth on the seating unit that rests on the ground with a convex side.

An advantage of these movement detectors is that each of these movements is detectable and can be reported to the central learning module via the digital module.

BRIEF DESCRIPTION OF THE DRAWINGS

With the intention of better showing the characteristics of the invention, a few preferred embodiments of the device for linking bodily movement to learning behaviour according to the invention are described hereinafter, by way of an example without any limiting nature, with reference to the accompanying drawings, wherein.

DETAILED DESCRIPTION OF THE PREFERRED EMBODIMENTS

Figure 1:
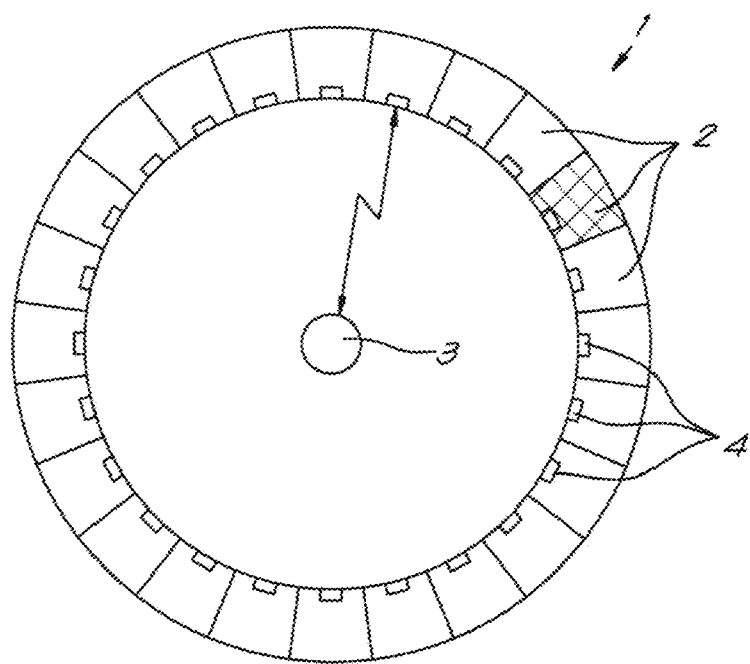
FIG. 1 schematically shows a top view of a device for linking bodily movement to learning behaviour according to the invention.

FIG. 1 shows a top view of a device for linking bodily movement to learning behaviour according to the invention. The device 1 consists of a number of individual seating units 2, which in this case are placed against one another to form a circle around a central teaching module 3. Each seating unit is equipped with a digital module 4 that can communicate wirelessly with the central teaching module 3.

Figure 2:
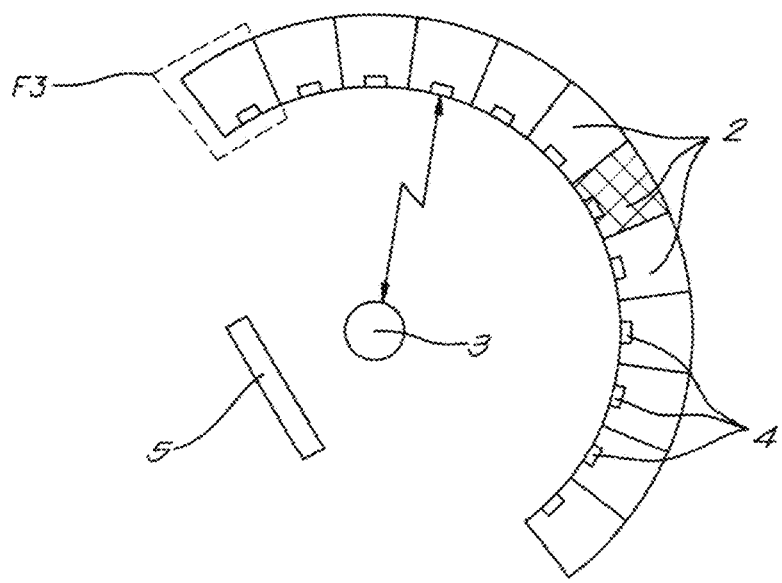
FIG. 2 shows a variant arrangement of FIG. 1.

FIG. 2 shows a variant of FIG. 1, whereby in this case the seating units are arranged in a semicircle around the central teaching module 3. In this arrangement a board 5 can be placed behind the central teaching module 3 that can be seen from each seating unit.

Figure 3:
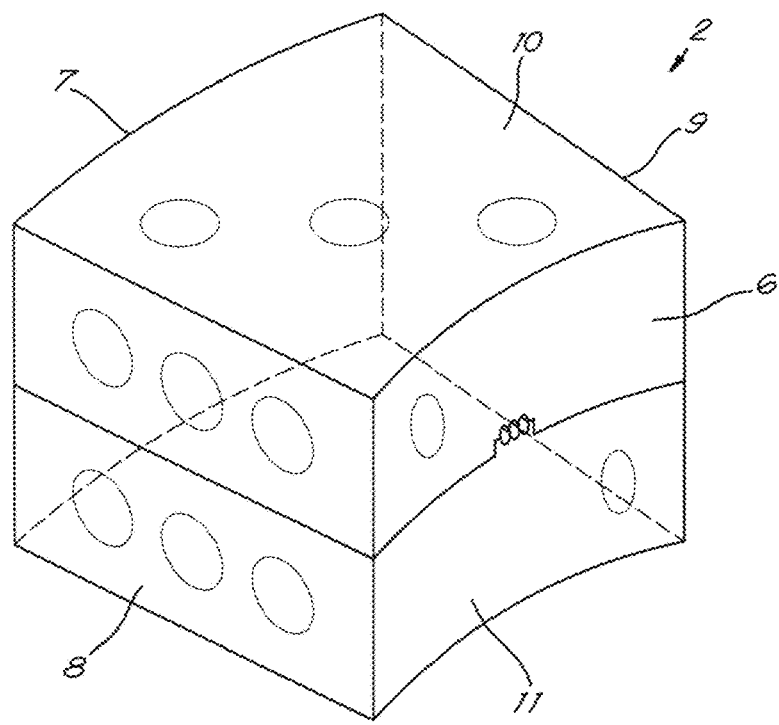
FIG. 3 shows a perspective view in more detail of one seating unit indicated by F3 in FIG. 1.

FIG. 3 shows a perspective view in more detail of one seating unit 2, in this case in the form of an irregular cube, with a concave face 6 and a convex face 7, connected by four flat faces 8, 9, 10, 11.

Figure 4:
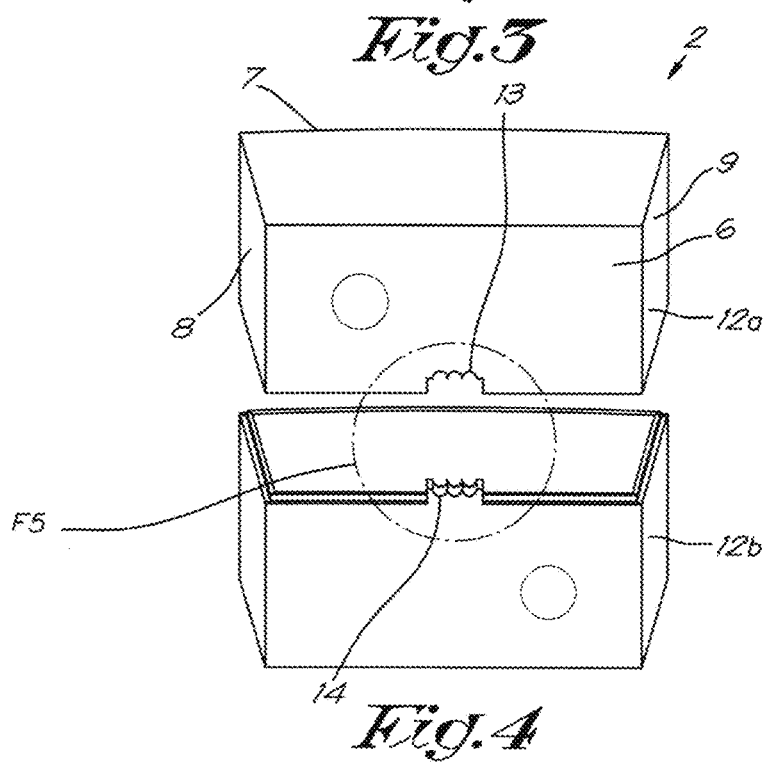
FIG. 4 shows a perspective view of the seating unit of FIG. 3 but now with its two constituent parts moved apart.

FIG. 4 shows a perspective view of the seating unit of FIG. 3 but now with its two composite parts 12a, 12b moved apart. In the central section F5 of the concave face 6, a recess 13 is provided in the top section 12a that engages with a protrusion 14 in the bottom section 12b with the formation of a suitable space in which a digital module 4 can be placed.

Figure 5:
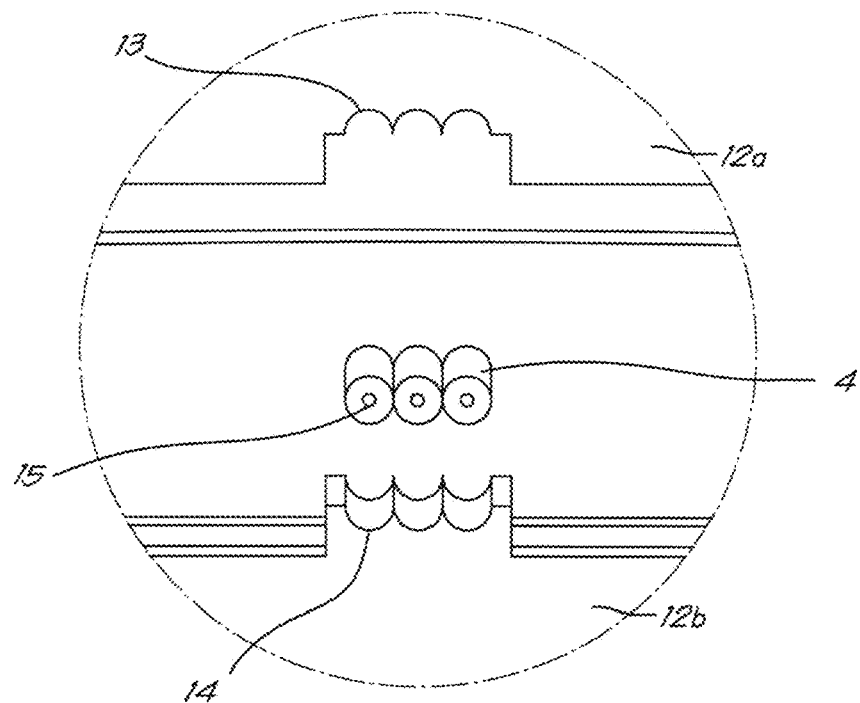
FIG. 5 shows the central section indicated by F5 of the concave face of FIG. 4 in more detail.

FIG. 5 shows the central section of the concave face 6 of FIG. 4 in more detail, with the recess 13 in the top section 12a of the irregular cube and the protrusion 14 in the bottom section 12b of the irregular cube, between which a suitable digital module 4 can be placed, equipped with LED light sources 15.

Figure 6:
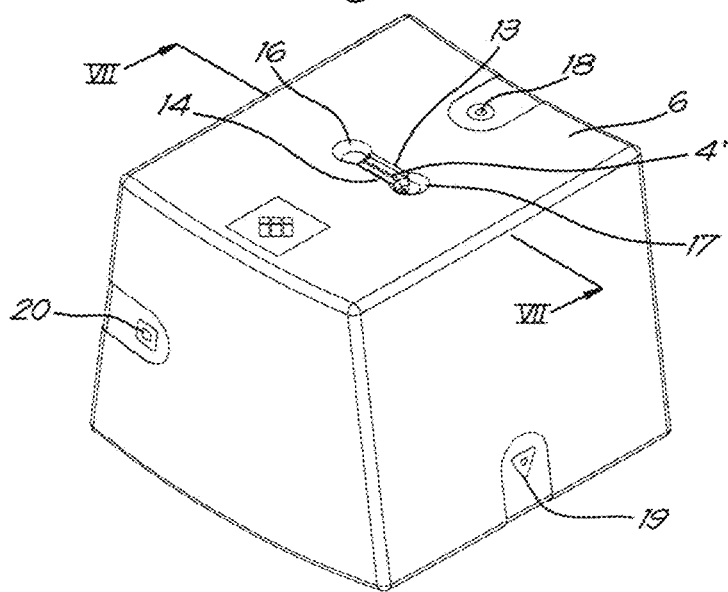
FIG. 6 shows a variant of FIG. 3.

FIG. 6 shows a perspective view of a variant embodiment of FIG. 3, whereby in addition to the recesses 13, 14 in the centre of the concave face 6 of the seating unit 2 for the insertion of the digital module 4', two extra recesses 16, 17 are also provided that act as a handle. The faces of the seating unit are also provided with different symbols 18, 19, 20 whereby each face can be identified.

Figure 7:
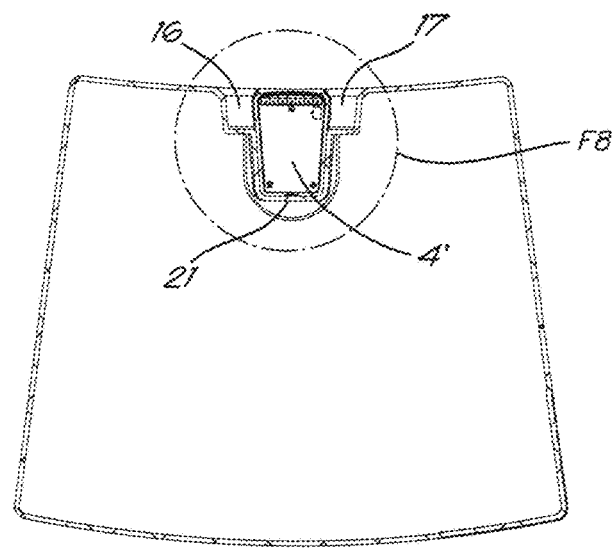
FIG. 7 shows a cross-section according to line VII-VII of FIG. 6.

FIG. 7 shows the cross-section according to line VII-VII of FIG. 6, on which the cross-section of the cavity 21 can be seen in which the digital module 4' is held, as well as the two extra recesses 16, 17 for the handle.

Figure 8:
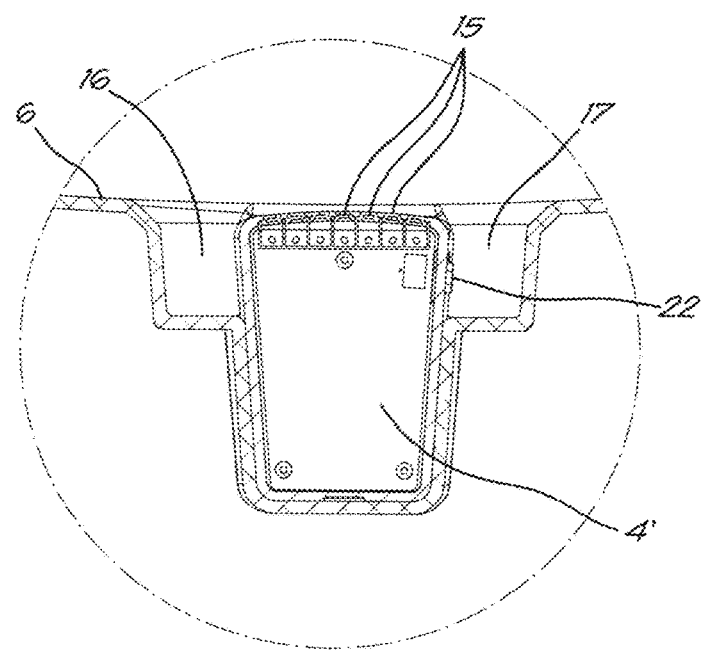
FIG. 8 shows the section indicated by F8 in FIG. 7 in more detail.

FIG. 8 shows the section of FIG. 7 in more detail, indicated by F8, where it can be seen that one of the two extra recesses 17 also enables the switch 22 to be accessed for switching the digital module on and off that is in the inserted position.

Figure 9:
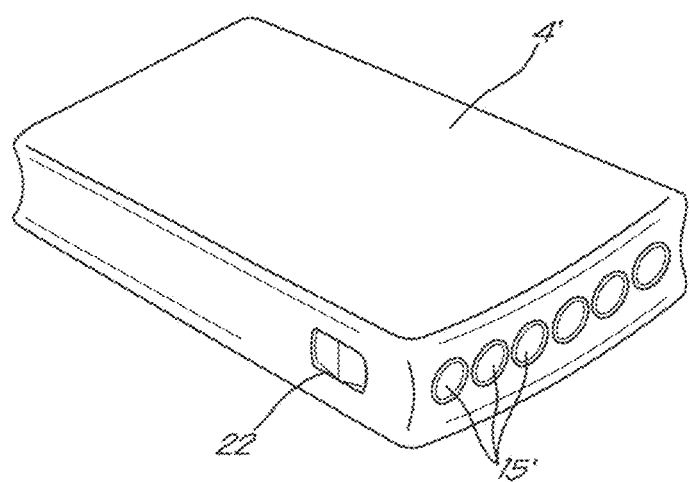
FIG. 9 shows a variant embodiment of the digital module.

FIG. 9 shows the variant of the digital module 4' in more detail that was used in FIG. 7. The variant is equipped with a series of LED light sources 15' on the face that is visible on the concave face of the seating unit 2, and with a switch 22 that can also be operated in the inserted position.

The method for using the device 1 for linking bodily movement to learning behaviour is simple and as follows.

A number of seating units 2 according to the invention are arranged in an arbitrary pattern according to choice in the available educational space, whereby a central teaching module 3 is wirelessly connected to the digital module 4 in each seating unit.

The teacher can set a task for the pupils who have sat down in the seating units 2, for example by setting a multiple choice question on a board 5, whereby the pupil can choose from three answers for example, of which one is correct.

The pupils can make their choice known by moving their seating unit, for example by turning a certain side of it upwards, whereby the digital module 4 in their seating unit will pass on the position or the movement of their seating unit to the central teaching module 3. The central teaching module 3 will now send an individual wireless signal to each seating unit 2, consisting of an identification of the seating unit 2 for which the message is intended, followed by an evaluation of the individual answer given from the seating unit 2 concerned, for example whether the answer was right or wrong or another evaluation of the answer, and will provide an individual light signal on each seating unit 2, from which the pupil can read on his seating unit 2 whether his answer was right or wrong or what evaluation he received for it.

The pupil can communicate with the central teaching module 3 with his seating unit in other ways, by sending different messages by throwing the seating unit in the air for example, or rocking the seating unit, whereby a certain message is attached to each movement such as for example: I don't know, or I need more explanation, etc.

The intention is to couple the learning experience to physical activity by the pupil, which fosters the learning process. Three types of exercise can help here:

1) Bodily movement that increases the heart rate of the pupil for at least five minutes, for example;

2) Bodily movement that consists of small intervals of physical activity, whereby some physical intensity can be coupled to cognitive challenges or otherwise, such as answering questions;

3) Bodily movement that fosters the learning of a specific subject.

The seating unit 2 can be utilised for these three types of bodily movement in an educational environment, such as the space of a classroom or a gymnasium for example.

The aim is always to supply fresh oxygen to the brain of the pupil and to create variety in teaching.

It goes without saying that a number of variants of this method is possible, making use of the same seating elements 2 provided with digital modules 4.

Thus the number of types of assignments for the pupils is practically inexhaustible and other types of movement can also be utilised as a signal given from and by the pupils.

The assignments are not limited to the multiple choice question from which a good answer must be selected, or to receiving a right or wrong message, but other assignments or questions can also be set whereupon a personal evaluation can be sent to each individual seating unit and thus to the pupil associated with it.

Thus the seating elements 2 can also take on the form of an object on which the pupils have to stand, or which they have to keep under their arm, etc. It is important that they provide information through the movement of these objects to the central teaching module, and simultaneously are spurred on to bodily movement.

The present invention is by no means limited to the embodiments described as an example and shown in the drawings, but a device for linking bodily movement to learning behaviour according to the invention can be realised in all kinds of forms and dimensions without departing from the scope of the invention, as defined in the following claims.

The invention claimed is:

1. A method for linking seat movement to learning behavior, the method comprising:
    providing an arrangement of a plurality of objects that are cube-shaped seating units in an arbitrary pattern around the central teaching module that is wirelessly connected to a digital module in each cube-shaped seating unit, the digital module being configured to detect movements of the respective cube-shaped seating unit caused by the pupils to answer questions or assignments;
    transmitting, by the digital module in the respective cube-shaped seating unit, the position or the movement of the respective cube-shaped seating unit wirelessly to the central teaching module when the pupils give an answer to an assignment by moving the respective cube-shaped seating unit; and
    sending an individual wireless signal by the central teaching module to each cube-shaped seating unit related to the movement that is made with the respective cube-shaped seating unit, the individual wireless signal including an identification of the cube-shaped seating unit for which the individual wireless signal is intended, evaluating an individually-provided answer from the cube-shaped seating unit to which the individual wireless signal is sent as to whether the answer was right or wrong or providing another evaluation of the answer, and providing an individual light signal on each cube-shaped seating unit from which the pupil can read at the respective cube-shaped seating unit whether the answer was right or wrong, or an indication of the other evaluation of the answer,
    wherein each of the cube-shaped seating units is equipped with one or more of movement detectors and orientation detectors that are connected to the digital module of the respective cube-shaped seating unit to detect the movement and the position of the respective cube-shaped seating unit, and
    the method further comprises transmitting, by the movement detectors and the orientation detectors, the movements and the positions caused by the pupil to answer questions or assignments to the digital module of the respective cube-shaped seating unit.

2. The method according to claim 1, wherein the individual wireless signal is responsive to the movement that is made with each of the cube-shaped seating units.

3. The method according to claim 1, wherein each of the cube-shaped seating units is equipped with one or more light sources, and
    the method further comprises switching on or off the one or more light sources by the central teaching module, a color of the one or more light sources being able to be changed by the central teaching module.

4. The method according to claim 1, wherein the cube shape of the seating units is not fully symmetrical but has one convex side and one concave side opposite the one convex side of the cube.

5. The method according to claim 1, further comprising:
    detecting, by the movement detectors of each of the cube-shaped seating unit, which side of the cube-shaped seating unit is oriented upwards.

6. The method according to claim 1, further comprising:
    detecting, by the movement detectors of each of the cube-shaped seating unit, whether the cube-shaped seating unit is knocked by hand or foot.

7. The method according to claim 1, further comprising:
    detecting, by the movement detectors of each of the cube-shaped seating unit, a number of times the cube-shaped seating unit has been knocked.

8. The method according to claim 1, further comprising:
    detecting, by the movement detectors of each of the cube-shaped seating unit, whether the cube-shaped seating unit is thrown in the air by free-fall detection.

9. The method according to claim 1, further comprising:
    detecting, by the movement detectors of each of the cube-shaped seating unit, whether the cube-shaped seating unit is shaken and the number of times the cube-shaped seating unit is shaken.

10. The method according to claim 1, further comprising:
    detecting, by the movement detectors of each of the cube-shaped seating unit, whether the cube-shaped seating unit is rocking back and forth.

11. The method according to claim 1, wherein the cube-shaped seating units are configured to be manipulated directly by the pupils.

12. The method according to claim 1, wherein the cube-shaped seating units are configured to be manipulated in various positions of the respective cube-shaped seating units by the pupils.

* * * * *